United States Patent
Amara et al.

(10) Patent No.: US 6,783,554 B2
(45) Date of Patent: Aug. 31, 2004

(54) PILE MESH PROSTHESIS

(75) Inventors: Ryan A. Amara, Lynn, MA (US);
Peter H. Gingras, Windham, NH (US);
Theodore Karwoski, Hollis, NH (US);
Steve A. Herweck, Nashua, NH (US)

(73) Assignee: Atrium Medical Corporation, Hudson, NH (US)

( * ) Notice: Subject to any disclaimer, the term of this patent is extended or adjusted under 35 U.S.C. 154(b) by 0 days.

(21) Appl. No.: 09/789,333

(22) Filed: Feb. 20, 2001

(65) Prior Publication Data

US 2002/0116070 A1 Aug. 22, 2002

(51) Int. Cl.[7] .................................................. A61F 2/02
(52) U.S. Cl. ................ 623/23.76; 623/1.52; 623/23.74; 606/151
(58) Field of Search ................................ 623/1.5, 1.52, 623/23.72, 23.74, 23.76, 1.3, 11.11; 606/151

(56) References Cited

U.S. PATENT DOCUMENTS

| | | | |
|---|---|---|---|
| 2,671,444 A | 3/1954 | Pease | 128/82 |
| 3,054,406 A | 10/1959 | Usher | 128/334 |

(List continued on next page.)

FOREIGN PATENT DOCUMENTS

| | | | | |
|---|---|---|---|---|
| DE | 416327 | | 7/1925 | |
| DE | 20218798 U1 | * | 2/2003 | ............. A61F/2/02 |
| EP | 0 898 944 | | 3/1999 | |
| JP | 2000080541 A | * | 3/2000 | ........... D04B/21/02 |
| WO | WO 98/37813 | | 9/1998 | |
| WO | WO 99/05990 | | 2/1999 | |

OTHER PUBLICATIONS

Caneiro et al., Pub. No.: US 2001/0056303 A1.*

Primary Examiner—Corrine McDermott
Assistant Examiner—Javier G. Blanco
(74) Attorney, Agent, or Firm—Lahive & Cockfield, LLP (57) ABSTRACT

A method and apparatus relating to a biocompatible soft tissue implant is disclosed. The implant, in the form of a prosthesis, is constructed of a knitted pile mesh material arranged into either a 3-dimensional structure or a planar shape or structure. The material or fabric includes a plurality of filament extensions projecting outwardly therefrom. The filament extensions can be radially projecting looping filaments from one or more rows of the knitted pile mesh material. The combination of the filament extensions with the 3-dimensional structure results in the biocompatible implant having a structural resistance to hinder anticipated crushing forces applied to the implant, and also provide a suitable 3-dimensional structure for promoting rapid tissue in-growth to anchor such implant without migration and strengthen the repaired tissue area.

19 Claims, 5 Drawing Sheets

U.S. PATENT DOCUMENTS

| | | | | |
|---|---|---|---|---|
| 3,124,136 A | | 3/1964 | Usher | 128/334 |
| 3,878,565 A | * | 4/1975 | Sauvage | 623/1.5 |
| 4,047,252 A | * | 9/1977 | Liebig et al. | 623/1.5 |
| 4,347,847 A | | 9/1982 | Usher | 128/334 |
| 4,452,245 A | | 6/1984 | Usher | 128/334 |
| 4,695,280 A | * | 9/1987 | Watanabe et al. | 623/1.54 |
| 4,769,038 A | | 9/1988 | Bendavid et al. | 623/13 |
| 4,839,215 A | | 6/1989 | Starling et al. | 428/131 |
| 5,002,583 A | * | 3/1991 | Pitaru et al. | 623/11.11 |
| 5,116,357 A | | 5/1992 | Eberbach | 606/213 |
| 5,141,515 A | | 8/1992 | Eberbach | 606/151 |
| 5,147,374 A | | 9/1992 | Fernandez | 606/151 |
| 5,178,630 A | * | 1/1993 | Schmitt | 623/1.52 |
| 5,254,133 A | | 10/1993 | Seid | 606/215 |
| 5,292,328 A | | 3/1994 | Hain et al. | 606/151 |
| 5,356,432 A | | 10/1994 | Rutkow | 623/11 |
| 5,397,331 A | | 3/1995 | Himpens et al. | 606/151 |
| 5,456,720 A | | 10/1995 | Schultz et al. | |
| 5,569,273 A | | 10/1996 | Titone et al. | 606/12 |
| 5,593,441 A | | 1/1997 | Lichtenstein et al. | 623/151 |
| 5,614,284 A | | 3/1997 | Kranzler et al. | 428/138 |
| 5,634,931 A | | 6/1997 | Kugel | 606/151 |
| 5,674,276 A | * | 10/1997 | Andersen et al. | 623/1.5 |
| 5,711,960 A | | 1/1998 | Shikinami | 424/426 |
| 5,716,408 A | | 2/1998 | Eldridge et al. | 623/11 |
| 5,725,577 A | | 3/1998 | Saxon | 623/11 |
| 5,733,337 A | | 3/1998 | Carr, Jr. et al. | 623/11 |
| 5,769,864 A | | 6/1998 | Kugel | 606/151 |
| 5,858,505 A | | 1/1999 | Moen et al. | 428/131 |
| 5,916,225 A | | 6/1999 | Kugel | 606/151 |
| 5,919,232 A | | 7/1999 | Chaffringeon et al. | 623/11 |
| 5,954,767 A | | 9/1999 | Pajotin et al. | 623/11 |
| 5,990,378 A | | 11/1999 | Ellis | 623/11 |
| 6,031,148 A | | 2/2000 | Hayes et al. | 623/11 |
| 6,090,116 A | | 7/2000 | D'Aversa et al. | 606/151 |
| 6,090,137 A | | 7/2000 | Schmitt | 623/1.44 |
| 6,113,641 A | | 9/2000 | Leroy et al. | 623/23.075 |
| 6,120,539 A | | 9/2000 | Eldridge et al. | 623/11.11 |
| 6,165,217 A | | 12/2000 | Hayes | 623/11.11 |
| 6,166,286 A | | 12/2000 | Trabucco | 623/11 |
| 6,224,616 B1 | | 5/2001 | Kugel | 606/151 |
| 6,443,964 B1 | | 9/2002 | Ory et al. | 606/151 |
| 6,447,551 B1 | * | 9/2002 | Goldmann | 623/23.76 |
| 6,547,820 B1 | * | 4/2003 | Staudenmeier | 623/1.49 |

\* cited by examiner

PILE MESH PROSTHESIS

FIELD OF THE INVENTION

The invention relates to an implantable prosthesis material suitable for repairing muscle or tissue wall defects. It can be used for supporting, reinforcing, anchoring, and stabilizing tissue due to trauma, naturally occurring defects, herniation, cancer and/or surgical intervention.

BACKGROUND OF THE INVENTION

A multitude of surgical procedures today utilize prior art flat synthetic implant fabric materials to help support, anchor, and stabilize soft tissue. A soft tissue patch is an example of a flat fabric synthetic implant commonly used for such purposes. A variety of raw materials and polymers including bovine sourced collagen, polypropylene, nylon, polyester, and expanded polytetrafluoroethylene (PTFE) are used to form flat synthetic fabrics. Various manufacturing processes take these raw materials and form them into different fabric or laminate structures. The most popular synthetic soft tissue implant is constructed of a smooth open mesh fabric structure. Since the mid 1950's, polypropylene mesh fabrics have been used for soft tissue repair because the uniform open-pore structure encourages rapid cell penetration during healing. This in-growth through a porous mesh fabric adds to the strength of the surgical repair while the mesh provides a trellis for tissue anchoring and mechanical reinforcement to the healed repair following surgery.

Surgeons utilize synthetic meshes to repair, for example, hernias. A hernia is an abnormal protrusion of an organ, tissue, or any other anatomical structure, through a weakened area or opening in a surrounding or adjacent tissue wall. Hernias most often occur in the inguinal region near the bottom of the abdominal cavity. The abdominal muscle and connective tissue wall in the inguinal region on both right and left sides of individuals can often be weaker than surrounding muscle wall, hence, the high incidence of herniation in this area of the body. A portion of intestine or other abdominal cavity tissue extrudes through the weak spot in the surrounding tissue. Under physical pressure from daily activities, for example, a section of the intestine can push the thin peritoneum membrane, which is a protective membrane that lines the abdominal cavity. The tissue typically does not tear the peritoneum, thus when the tissue protrudes, the peritoneum covers the tissue. The term "hernial sac" describes the peritoneal covering surrounding the piece of protruding tissue.

One known surgical technique to treat the hernia and eliminate the protrusion, is to make an incision in the skin, followed by dissection through the subcutaneous fat and external oblique muscle to reach the forced opening in the abdominal wall. The surgeon usually dissects free and pushes that portion of the peritoneum covered organ extending through the rupture back through the defect to the proper side of the abdominal cavity. The repair can continue by pulling the edges of the rupture together and suturing or stapling them closed. This procedure is often limited to smaller type hernias and requires careful operative care to prevent tension on the fragile tissues. Tension on such tissues can result in substantial patient discomfort, and can result in recurrence or re-herniation of the same tissue. This type of repair relies solely on the structural integrity of the connective tissue to contain and prevent the hole from reforming.

Another known surgical technique for repairing a hernia defect utilizes a biocompatible prosthetic constructed from, for example, a flat polypropylene mesh fabric. After pushing the protruding organ back through the defect, the surgeon places a piece of flat mesh or PTFE fabric on one side of the muscle wall, bridging the opening or rupture without pulling the tissues back together. This is referred to as a tension free hernia repair. Hence, use of a prosthetic mesh or PTFE fabric helps stabilize the open defect by providing a trellis for tissue to grow into, and through, without tension on the surrounding natural tissue. This repair is known to produce a lower incidence of reoccurrence of the hernia with the use of prosthetic mesh fabric implants.

Still another known prosthetic hernia technique is the use of a folded or pre-shaped flat mesh fabric placed as a plug, rather than a flat patch. If the tissue opening or rupture is relatively small, the surgeon can alternatively roll up, fold, or form the flat mesh fabric into a plug like tampon and insert it lengthwise into the defect, plugging the rupture. Cell tissue, over time, grows through and into the dense folded and formed plug to help hold and stabilize the plug in place. This particular plug technique can sometimes stabilize a defect mechanically with the addition of bulk material placed into the plane of weakened or ruptured tissue, which can aid in a more rapid patient convalescence and return to daily activity. However, since many hernia and tissue defects are non-symmetrical, not all flat mesh fabric plug shapes or preformed shapes uniformly fit the defect hole. Most preformed plugs constructed from flat mesh fabric must be appropriately sized to fit the size of the defect.

Whether a flat mesh fabric or a mesh fabric folded or formed into a 3-dimensional plug shape or structure, such prosthetic materials aid the surgeon in completion of a tension-free repair by eliminating the need to pull tissue structures together. Flat mesh fabric implants are frequently sutured over the hernia defect, thus preventing re-herniation by placing a barrier over the defect. A flat sheet or preformed flat piece of mesh fabric, in certain circumstances, does not sufficiently anchor, stabilize, or fill the hernia defect.

SUMMARY OF THE INVENTION

There exists in the art a need for a biocompatible surgical implantable prosthesis suitable for repairing, stabilizing, anchoring more completely, and filling of both naturally occlusive tissue defects, or open holes from trauma or cancer, while effectively promoting rapid tissue in-growth with less structural or material density. A more dense or less porous fabric results in a more pronounced foreign body reaction to the implant. The implant construction of the present invention provides more structural contact filling of a tissue hole or defect, with a more open and resilient 3-dimensional structure that enables quick healing, with a lower density and resultant tissue encapsulation.

A biocompatible soft tissue implant provided in accordance with one example embodiment of the present invention is a pile mesh prosthesis constructed of a plurality of strips of knitted pile mesh, interconnected by one or more monofilament connecting bridges. At least one row has a plurality of filament extensions projecting outwardly therefrom. The filament extensions, in accordance with one aspect of the present invention, are in the form of a plurality of filament loops that provide radial contact with tissue to stabilize the implant and provide resistance to compression or crushing forces applied to the prosthesis following implantation. Structurally, the rows of knitted pile mesh provide mechanical strength, compliance, and flexibility. The protruding loops, which extend radially from the rows, provide a structural tissue contact means minimizing direct contact of the knitted rows of mesh, thereby reducing the density of material to be healed after implant. The rows can be of a different foundational structure for supporting the filament extensions.

The pile mesh construction can fit into an irregularly shaped tissue hole or defect and completely fill the area as a material plug, with significantly less material mass than a traditional flat mesh fabric or patch. Such an open pile mesh prosthesis provides a relatively lighter, less dense, structural hole filler facilitating more rapid healing. Biomaterial evidence indicates that less plastic results in less inflammation, and less mass requires less cell remodeling to achieve full tissue stabilization and prevent encapsulation. The pile mesh prosthesis of the present invention, due to its 3-dimensional filament configuration, also helps to stabilize the implant in a more fixed, less likely to migrate, condition relative to current known flat mesh fabric devices. The overall radial compression resistance of the loop filament extensions, together with the multiple rows of the knitted mesh, provides a more uniformly fitting prosthesis for a preferred tension free prosthetic repair. The inventive device requires less orientation by the surgeon during placement because of the self-centering action of the radially protruding loops.

Aspects of the present invention provide unique tissue contact for healing and stabilization without the need for excessive laminations or flat material bulk. The pile mesh prosthesis device employs relatively less material bulk, or mass, and maintains good contact surface geometric area. The pile mesh prosthesis can further have an organized 3-dimensional structure that can provide a relatively large external dimensional volume, with a relatively small weight, or amount, of plastic. The pile mesh structure is a relatively elastic structure having a plurality of structural elements forming an interior thereof. The structure is substantially compressible, while maintaining a shape memory. The overall structure is lighter than equivalently sized and shaped flat mesh fabric constructions.

The biocompatible implant, according to one aspect of the present invention, has a plurality of rows of knitted mesh material, a portion of which form at least two distinct rows. A plurality of connecting bridges couples the rows. The at least two rows further include a plurality of filament loop extensions projecting outwardly therefrom.

The filament extensions, in accordance with still other aspects of the present invention, can be either substantially uniform in projection distance, or of unequal heights or lengths from the knitted rows of material.

The biocompatible implant, in accordance with still another aspect of the present invention, has the pile mesh material permanently arranged in a 3-dimensional shape or structure, such as, e.g., a tube, pyramid, or hexagon, suitable for conforming to a specific tissue defect anomaly. A gathering of the rows of loop mesh arranged within a 3-dimensional structure shape or structure can also provide additional radial support structure, without adding mass to the implant.

BRIEF DESCRIPTION OF THE DRAWINGS

The aforementioned features and advantages, and other features and aspects of the present invention, will become better understood with regard to the following description and accompanying drawings, wherein.

DETAILED DESCRIPTION OF THE INVENTION

The present invention generally relates to an improved surgical structure for repairing hernias, abdominal walls, chest walls, and other soft tissue defects. An implantable prosthesis material, as a planar patch, preformed into an anatomical shape, or formed into a uniform shape plug configuration, is constructed from a polypropylene monofilament, which provides a framework for new tissue growth to support the soft tissue repair. The implantable prosthesis contains a raised surface comprised of a plurality of filament extensions that extend a minimum of one-third of a knitted row mesh cross-sectional depth. The filament extensions can be in the form of multiple pile loops of polypropylene monofilament or multifilament yarns. The pile loops provide a substantial amount of radially supported surface area, which allows for more complete filling of the soft tissue defect without a bulky flat fabric mass. The pile mesh loops provide additional tissue contact surface area for promoting tissue healing and remodeling induced by the foreign body reaction of the polymer prosthetic material. The implantable prosthesis of the present invention has the advantage of conforming to the defective anatomy due to the inherent properties of the mesh structure. This can minimize or eliminate the need for pre-cut or pre-shaped sizes commonly required with flat mesh fabric prostheses.

FIGS. 1 through 13, wherein like parts are designated by like reference numerals throughout, illustrate example embodiments of an implantable prosthesis according to the present invention. Although the present invention will be described with reference to the example embodiments illustrated in the figures, it should be understood that many alternative forms can embody the present invention. One of ordinary skill in the art will additionally appreciate different ways to alter the parameters of the embodiments disclosed. The alterations can address the size, shape, or type of elements or materials, in a manner still in keeping with the spirit and scope of the present invention.

Figure 1:
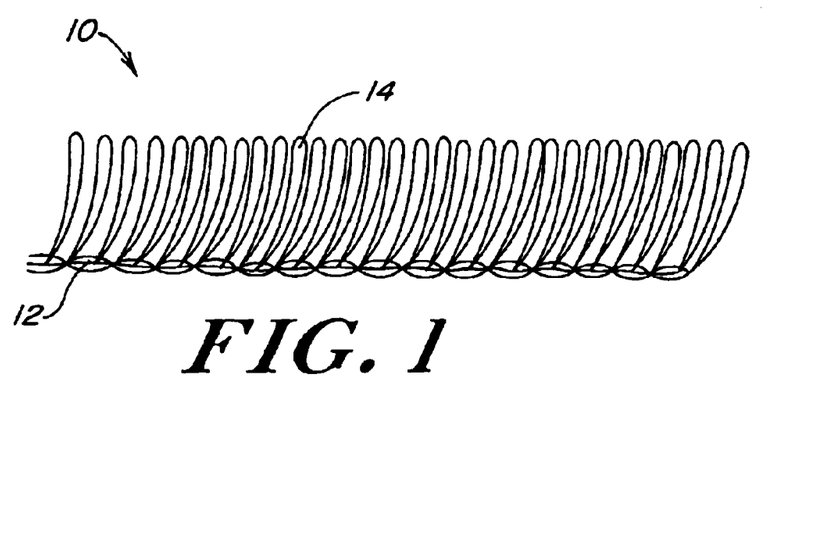
FIG. 1 is a side view of an implantable prosthesis material according to one embodiment of the present invention.

A knitted mesh row 12 forms a foundation structure of an implantable prosthesis material 10, illustrated in FIG. 1. A polypropylene monofilament, in accordance with one aspect of the present invention, forms the knitted mesh row 12. In a preferred embodiment, the polypropylene monofilament is a 0.006-inch medical grade polypropylene monofilament. A knitting process forms the knitted mesh rows 12 into a relatively tight-knit mesh structure, however each knitted mesh row 12 can be made according to any number of different knitting patterns of both tight and loose constructions. The knitted mesh rows 12 are elongate, forming a long and narrow structure. However, the rows can be of any number of different shapes or structures depending partially on the desired application. The rows can be as narrow as a single strand of monofilament providing the foundational structure from which a plurality of filament extensions projects outward. The arrangement of the rows can also vary from, e.g., being substantially parallel, to non-parallel, rectilinear or non-rectilinear, crisscrossing, weaving, and the like.

The implantable prosthesis material 10 further includes a plurality of filament extensions in the form of extended filament loops 14 radiating in a generally orthogonal direction from the knitted mesh row 12. The knitting process also forms this plurality of extended filament loops 14, however other extended filament structures (e.g., circles, triangles, squares, individual strings, or other closed or open shapes or structures) are possible. The plurality of filament extensions, in this instance filament loops 14, can extend a substantially uniform distance from the knitted mesh row 12, but can alternatively extend in varying lengths along the rows of knitted material. Each of the plurality of extended filament loops 14 is flexibly resilient to external forces placed on the loops 14 in a compressive fashion toward the knitted mesh rows 12. The extended filament loops 14 have sufficient shape memory to keep the prosthesis in position while withstanding anticipated compressive forces applied in a body tissue environment.

Figure 2:
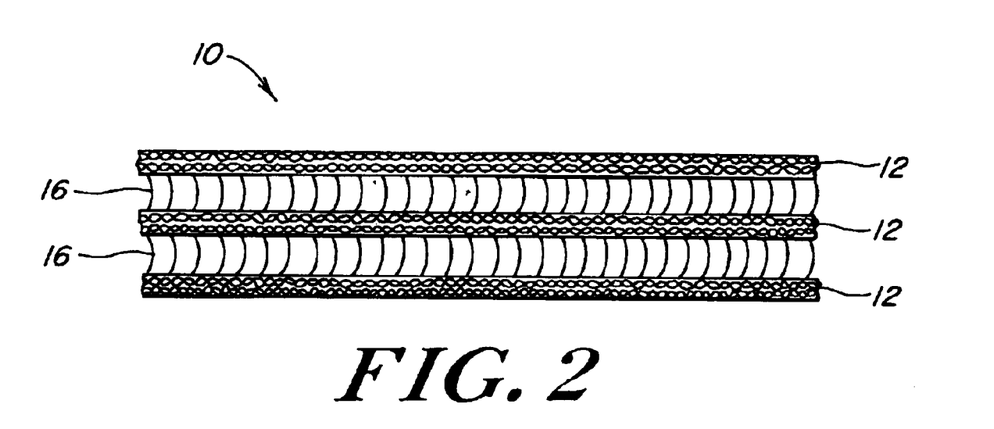
FIG. 2 is a bottom view of the implantable prosthesis material of FIG. 1.

FIG. 2 illustrates a bottom view of the implantable prosthesis material 10 of FIG. 1. The implantable prosthesis material 10, in accordance with the illustrative embodiment, has three knitted mesh rows 12 coupled with a plurality of crossing filament bridges 16. The knitting process also forms the plurality of crossing filament bridges 16, which extend laterally from each of the knitted mesh rows 12 and in a generally perpendicular direction from the extended filament loops 14. Each of the filament bridges 16 serves to couple each of the knitted mesh rows 12 together to maintain the knitted mesh rows 12 in a generally parallel or planar arrangement. Although the knitted mesh rows 12 generally reside in the particular arrangement desired, the filament bridges 16 maintain the ability to flexibly yield upon application of a crushing force applied to the prosthesis material 10. This allows each of the knitted mesh rows 12 to move relative to each other, and further allows the knitted mesh rows 12 to collapse toward each other under a sufficient crushing force.

The knitting process can arrange the filament bridges 16 in a variety of orientations, such as diagonal, zigzag, crosshatched, random, randomly intersecting, and the like, as long as the resulting filament bridges 16 couple the knitted mesh rows 12 together as one structure. The plurality of filament bridges 16 in each arrangement can further couple the knitted mesh rows 12 in any number of non-parallel and or alternating mesh row arrangements.

There can be a plurality of knitted mesh rows 12 of a number ranging from one to a maximum depending on the desired overall size of material 10. There can be any number of constructions for the arrangement of the knitted mesh rows 12 other than the parallel arrangement illustrated. The knitting process can, for example, form the knitted mesh rows 12 into non-linear row shapes, such as curves, approximate sine waves, zigzag patterns, random non-linear patterns, and the like.

The knitting process can construct the implantable prosthesis material 10 in any number of shapes, patterns, and arrangements. Additional manufacturing steps can form the resulting implantable prosthesis material 10 into any number of correlating 3-dimensional structures. The term "3-dimensional" means a structure having dimensions of an approximate similar range or scale of length, height, and width.

Figure 3:
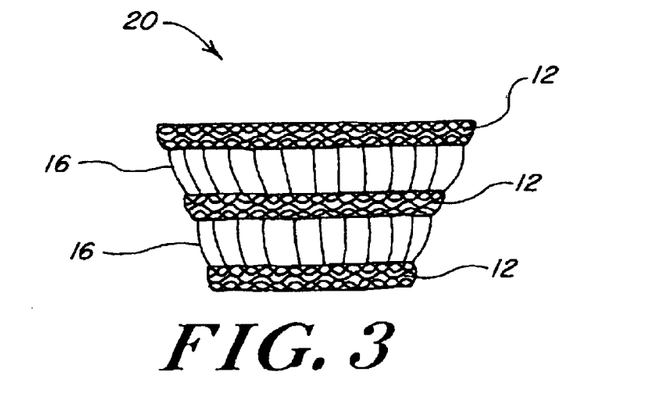
FIG. 3 is a side view of a conical implantable prosthesis according to one aspect of the present invention.

FIG. 3 illustrates one such 3-dimensional pile mesh structure. A swath of knitted pile mesh implantable prosthesis material forms a conical implantable prosthesis 20, a side view of which is illustrated in this figure. Several different processes and technologies can form the 3-dimensional shapes or structures, such as laser, heat forming, and cutting/welding technologies known to those of ordinary skill in the art. The basic process of taking a swath of the implantable prosthesis material 10, rolling the material 10, and connecting ends thereof, forms the generally conical construction of the conical implantable prosthesis 20. Each end of the knitted mesh rows 12 couples (e.g., utilizing laser, heat forming, and cutting/welding technologies) with an opposite end thereof forming a relatively seamless pre-formed shape. Each of the filament bridges 16 connects each of the knitted mesh rows 12 and aids in maintaining a desired distance between each of the knitted mesh rows 12. The structure of the filament bridges 16 allows an axial compression force to be placed on a tip of the conical implantable prosthesis 20 that does not substantially transmit to a base of the conical structure. The filament bridges 16, instead absorb such an axial force by flexing, hindering the force from translating throughout the conical implantable prosthesis 20 to the base. The result of this absorption action is that there is no perceptible distortion or widening of the base of the conical structure during such times as implantation of the prosthesis 20. The filament bridges 16 react similarly in other three-dimensional structures as well.

Figure 4:
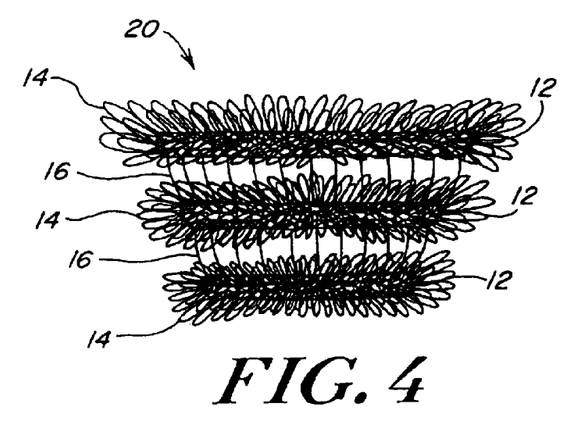
FIG. 4 is a side view of the conical implantable prosthesis of FIG. 3, further including a plurality of filament loops according to one aspect of the present invention.

FIG. 3 shows the basic structure underlying the conical implantable prosthesis 20, while FIG. 4 illustrates the conical implantable prosthesis 20 additionally having the plurality of extended filament loops 14 projecting outwardly from each of the knitted mesh rows 12. Several figures included herein show different underlying structures without the plurality of filament extensions to clearly disclose the underlying structures. Subsequent illustrations in each case show the same underlying structures with the addition of the filament extensions extending therefrom, in accordance with aspects of the present invention.

The extended filament loops 14 extend outwardly from the resulting 3-dimensional shape or structure to construct the conical implantable prosthesis 20. The flexible characteristics of the extended filament loops 14 provide a resistive force to anticipated external forces applied on the conical implantable prosthesis 20. It is often preferable in the design of implantable prosthesis structures to create a 3-dimensional structure that maintains a relatively large geometric shape (i.e., relatively large perimeter dimensions), while utilizing a minimal amount of polypropylene filament and having a relatively low density/specific gravity. The conical implantable prosthesis 20, according to the teachings of the present invention, achieves this characteristic in that it has relatively lower density/specific gravity than known implantable prosthesises having equivalent perimeter dimensional volume.

Figure 5:
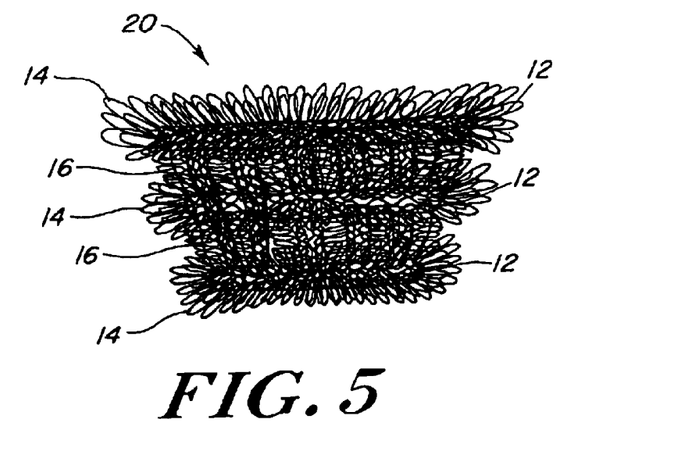
FIG. 5 is a side view of the conical implantable prosthesis of FIGS. 3 and 4, further including an internal gathering according to one embodiment of the present invention.
Figure 6:
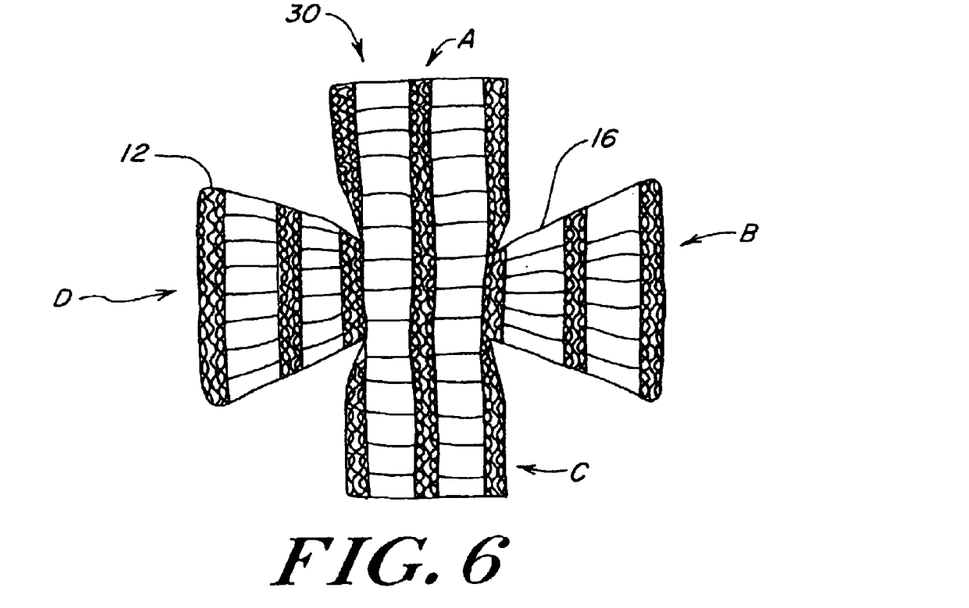
FIG. 6 is a top view of a single piece of implantable prosthesis material according to one aspect of the present invention.

FIG. 5 illustrates a further embodiment in the form of the generally conical implantable prosthesis 20 of FIGS. 3 and 4, including an internal material gathering 22 placed in an interior compartment of the 3-dimensional conical structure. The same type of implantable prosthesis material 10 of the generally conical implantable prosthesis 20 forms the internal structural gathering 22. Alternative materials and fabrics can also form the internal structural gathering 22 if desired. The internal structural gathering 22 aids the resistive characteristic of the extended filament loops 14. The internal structural gathering 22, in other words, provides added resistance to any external compressive forces on the conical implantable prosthesis 20, giving the conical implantable prosthesis bulkier geometric characteristics. The internal structural gathering 22 also further promotes tissue in-growth further into the 3-dimensional structure.

Figure 7:
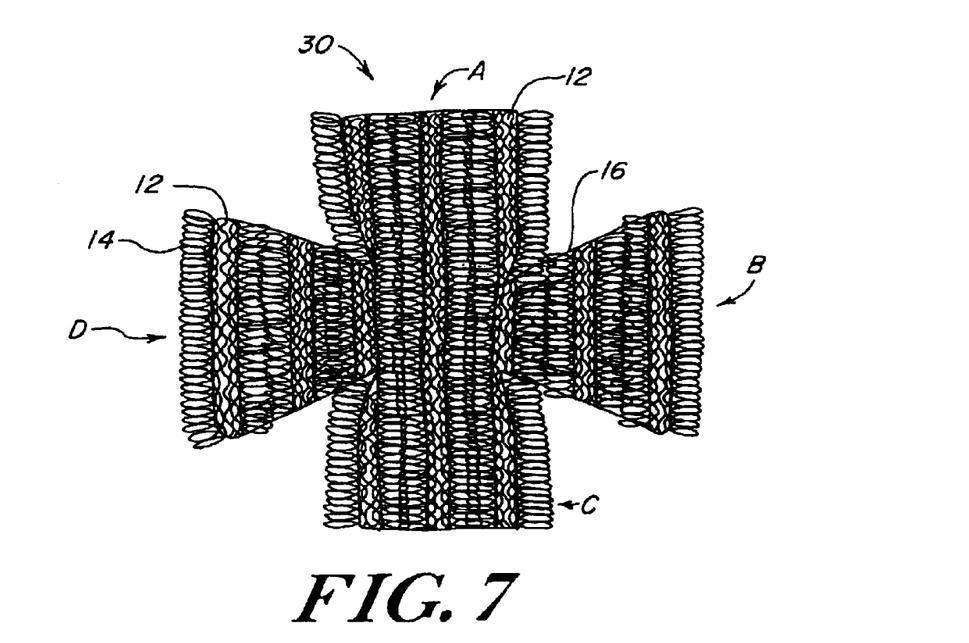
FIG. 7 is a top view of the material of FIG. 6, further including a plurality of filament extensions according to one aspect of the present invention.

FIGS. 6, 7, 8, and 9 illustrate a crisscross-shaped implantable prosthesis 30 that can serve as one possible approach to forming the generally conical implantable prosthesis 20 out of a single piece of implantable prosthesis material 10. The illustrative method begins with cutting a piece of implantable prosthesis material 10 into a crisscross shape or structure in the form of the crisscross-shaped implantable prosthesis 30. The crisscross-shaped implantable prosthesis 30 includes the plurality of knitted mesh rows 12 and extended filament loops 14 coupled together with the plurality of filament bridges 16. The crisscross shape has four ends, A, B, C and D. FIG. 7 shows the crisscross-shaped implantable prosthesis 30 further including the plurality of extended filament loops 14.

Figure 8:
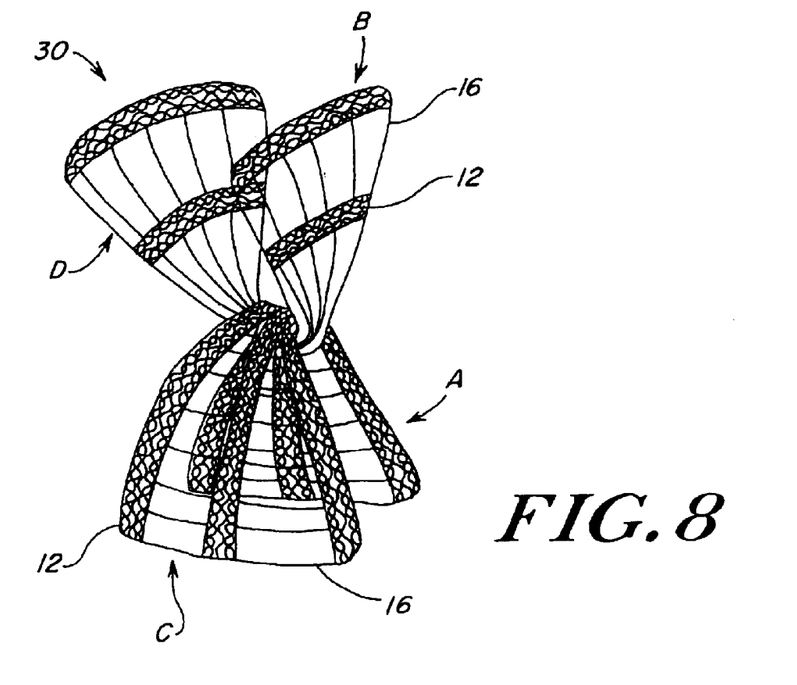
FIGS. 8 and 9 are perspective views of the material of FIGS. 6 and 7 respectively according to still another aspect of the present invention.
Figure 9:
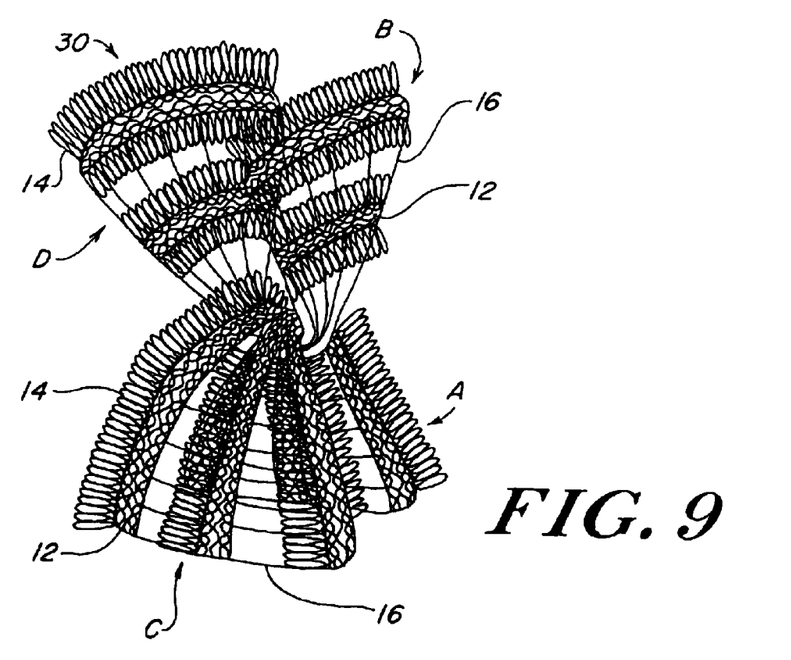

Each end, A, B, C and D, folds in a manner illustrated in accordance with the illustration of FIG. 8. Ends A and C fold downward toward each other, while ends B and D fold upward toward each other, or vice versa. FIG. 9 shows this folding arrangement with the added feature of the extended filament loops 14. Edges of the knitted mesh rows 12 join together (e.g., utilizing laser, heat forming, and cutting/ welding technologies) to form the conical structure of the conical implantable prosthesis 20 in previous figures, while the ends of B and D form the internal structural gathering 22. The ends B and D can also join, or can remain detached, while still forming the internal structural gathering 22. The conical structure folds back over the internal structural gathering 22, disposing the internal structural gathering 22 within an internal compartment or section of the conical structure to form the conical implantable prosthesis 20 of FIG. 5.

Figures 10, 11, 12, 13:
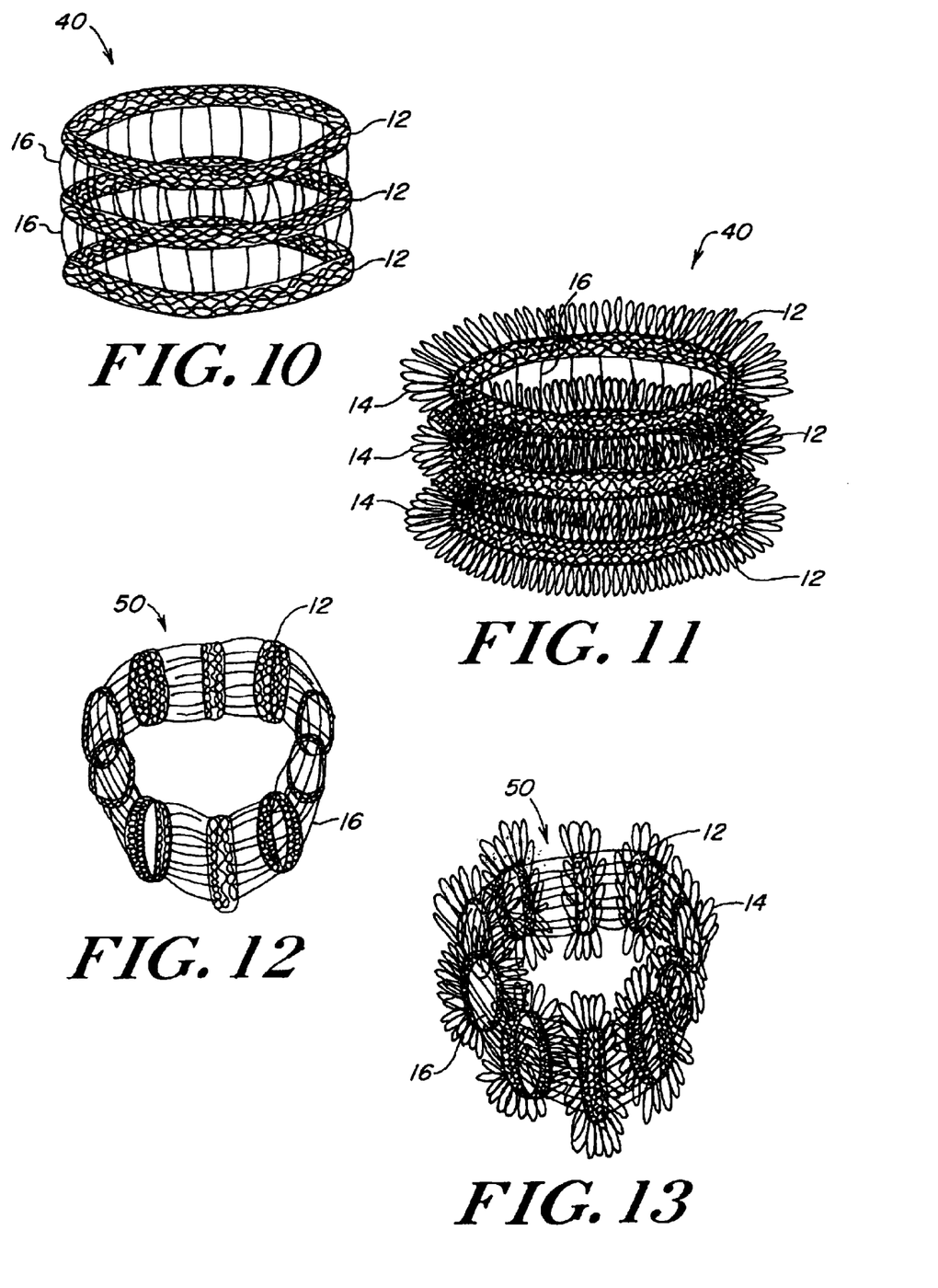
FIG. 10 is a perspective view of a cylindrical implantable prosthesis according to one embodiment of the present invention.
FIG. 11 is a perspective view of the cylindrical implantable prosthesis of FIG. 10, further including a plurality of filament extensions according to one embodiment of the present invention.
FIG. 12 is a perspective view of a tubular implantable prosthesis in accordance with one embodiment of the present invention.
FIG. 13 is a perspective view of the tubular implantable prosthesis of FIG. 12, further including a plurality of filament extensions according to one embodiment of the present invention.

FIGS. 10 and 11 illustrate another 3-dimensional arrangement. A generally cylindrical implantable prosthesis 40 has the plurality of knitted mesh rows 12 coupled by the plurality of filament bridges 16. The ends of the material join together to form the cylindrical shape. FIG. 11 shows the cylinder with the plurality of extended filament loops 14 projecting outwardly therefrom. An internal structural gathering (similar to the previous internal structural gathering 22) can insert into the interior portion of the cylindrical construct.

FIGS. 12 and 13 show yet another 3-dimensional structure formed by the implantable prosthesis material 10 according to the teachings of the present invention. A tubular implantable prosthesis 50 contains a plurality of knitted mesh rows 12 coupled to each other by a plurality of filament bridges 16. Steps of first rolling a piece of implantable prosthesis material, and then joining ends of the roll, form the tubular shape of the 3-dimensional tubular structure.

The various planar and 3-dimensional implantable prosthesis structures, according to the teachings of the present invention, can repair a rupture in a muscle wall according to at least two different methods. The first method involves the use of a swath or patch of implantable prosthesis material of any number of different shapes attached (e.g., sutured) to an area surrounding the rupture. The plurality of filament extensions presses against the muscle wall. The filament extension loop structure is highly effective at promoting tissue in-growth through a normal foreign body reaction to the monofilament material, which further anchors the material in place and promotes healing, anchoring, and prosthesis stabilization.

The second method involves the formation of the implantable prosthesis material into a 3-dimensional structure, such as those described herein. The 3-dimensional structure penetrates the muscle tissue rupture, providing support to the rupture walls and again promoting tissue in-growth to anchor the implantable prosthesis material in place while strengthening and healing the surrounding muscle tissue.

Any number of 3-dimensional shapes or structures can form an implantable prosthesis according to the teachings of the present invention. Alternatively, the implantable prosthesis material 10 can serve as a planar patch implant form, without further forming into a 3-dimensional structure. The present invention has the advantage of being able to completely fill a soft tissue void while minimizing the amount of material required. The 3-dimensional structure of both the implantable prosthesis material 10, and any resulting 3-dimensional structures formed thereof, provides maximum volume fill while utilizing a minimal amount of plastic polypropylene monofilament. The density/specific gravity of the 3-dimensional structures is approximately 50%, or one-half, the value of other known arrangements. Preformed plugs with less material cause less inflammation and scar tissue formation, which improves the biological response to the implant, allowing more efficient and thorough tissue in-growth. In addition, the rows of the prosthesis can be made of a polymeric material dissimilar to the extended loops or filament bridges. This can improve biocompatibility and tissue in-growth based on the anatomical location of the repair. For example, a synthetic absorbable material formed from the family of polymers known to degrade or be hydrolyzed in the body environment can be used to construct the entire prosthesis, or an individual element thereof.

Numerous modifications and alternative embodiments of the invention will be apparent to those skilled in the art in view of the foregoing description. Accordingly, this description is merely illustrative and for teaching those skilled in the art the best mode for carrying out the invention. Details of the structure may vary substantially without departing from the spirit of the invention, and exclusive use of all modifications that come within the scope of the appended claims is reserved. Only the appended claims and the applicable rules of law shall limit the scope of the present invention.

What is claimed is:

1. A biocompatible implant comprising:
a prosthesis constructed of at least two rows of knitted pile mesh material, wherein at least a portion of said at least two rows of knitted pile mesh material comprises a plurality of filament extensions that project radially and outwardly, wherein am least a portion of said two rows of knitted pile mesh material comprise at least one row of knitted pile mesh material joined to at least one additional row of knitted pile mesh material by am least one filament bridge.

2. The biocompatible implant according to claim 1, wherein said plurality filament extensions are formed of a plurality of looping filaments.

3. The biocompatible implant according to claim 2, wherein said plurality of looping filaments provide radial compression resistance, hindering a crushing force applied to said implant.

4. The biocompatible implant according to claim 2, wherein each of said plurality of looping filaments are substantially uniform in projection distance from said rows of knitted pile mesh material.

5. The biocompatible implant according to claim 1, wherein a plurality of monofilament bridges couple two or more rows of knitted pile mesh rows together.

6. The biocompatible implant according to claim 5, wherein said monofilament bridges flexibly yield upon application of a crushing force applied to said implant, allowing said two or more rows of knitted pile mesh to move relative to each other.

7. The biocompatible implant according to claim 6, wherein said flexible yielding of said monofilament bridges allows said two or more rows of knitted pile mesh to collapse toward each other.

8. The biocompatible implant according to claim 5, wherein said plurality of filament extensions are formed of a plurality of looping filaments that project outwardly from said two or more rows of knitted pile mesh material.

9. The biocompatible implant according to claim 8, wherein said plurality of looping filaments project outwardly from said two or more rows of knitted pile mesh material in a variably non-equidistant manner.

10. The biocompatible implant according to claim 5, wherein said knitted pile mesh material is formed into a 3-dimensional structure suitable for conforming to a tissue defect.

11. The biocompatible implant according so claim 10, wherein a gathering of said knitted pile mesh material is arranged internally within said 3-dimensional structure.

12. The biocompatible implant according to claim 10, wherein at least a portion of said plurality of filament extensions extend substantially orthogonal from a surface of said 3-dimensional structure.

13. The biocompatible implant according to claim 10, wherein said 3-dimensional structure is a generally conical arrangement.

14. The biocompatible implant according to claim 13, wherein said plurality of monofilament bridges flexibly yield upon application of a crushing force applied to said implant, allowing said two or more rows of knitted pile mesh so move relative to each other.

15. The biocompatible implant according to claim 14, wherein said flexible yielding of said plurality monofilament bridges allows said two or more rows of knitted pile mesh to collapse toward each other.

16. The biocompatible implant according to claim 10, wherein a substantially axial force placed on a lip of said conical arrangement causes said material to collapse toward a base of said conical arrangement without rigidly transmitting said axial force to said base.

17. The biocompatible implant according to claim 1, wherein said 3-dimensional structure comprises a generally conical arrangement having an internal material-gathering and said conical arrangement and internal material gathering are comprised of a single piece of said knitted pile mesh material.

18. The biocompatible implant according to claim 1, wherein said knitted pile mesh material is in a generally planar arrangement.

19. The biocompatible implant according to claim 1, wherein said filament extensions project sway from said at least one row of knitted pile mesh material.

* * * * *